US012694952B2

(12) United States Patent
Pande et al.

(10) Patent No.: US 12,694,952 B2
(45) Date of Patent: Jul. 28, 2026

(54) METHODS AND SYSTEMS FOR PREDICTING A REMAINING SHELF-LIFE OF A MILLET FLOUR USING DATA-DRIVEN APPROACH

(71) Applicant: Tata Consultancy Services Limited, Mumbai (IN)

(72) Inventors: Harshvardhan Pande, Pune (IN); Shrikant Arjunrao Kapse, Pune (IN); Shankar Balajirao Kausley, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 128 days.

(21) Appl. No.: 18/931,321

(22) Filed: Oct. 30, 2024

(65) Prior Publication Data

US 2025/0182860 A1 Jun. 5, 2025

(30) Foreign Application Priority Data

Dec. 2, 2023 (IN) .............................. 202321082073

(51) Int. Cl.
*G01N 33/02* (2006.01)
*G06N 3/0442* (2023.01)
(Continued)

(52) U.S. Cl.
CPC ........... *G16C 20/30* (2019.02); *G06N 3/0442* (2023.01); *G16C 20/70* (2019.02); *G06Q 10/087* (2013.01)

(58) Field of Classification Search
CPC ...... G16C 20/30; G16C 20/70; G06N 3/0442; G06Q 10/087
See application file for complete search history.

(56) References Cited

U.S. PATENT DOCUMENTS

2019/0050793 A1* 2/2019 Poolman ............ G06Q 10/0631
2020/0250531 A1* 8/2020 Rai ...................... G06N 3/0442
(Continued)

FOREIGN PATENT DOCUMENTS

WO 2023114121 A1 6/2023

OTHER PUBLICATIONS

Prasad Rasane et al., "Chemical Kinetic Modeling of Nutricereal based Fermented Baby Food for Shelf Life Prediction," Current Nutrition & Food Science, Dec. 2017, vol. 14; Issue: 0, Bentham Science Publishers https://www.researchgate.net/profile/Nitya-Sharma/publication/322089922_Chemical_Kinetic_Modeling_of_Nutricereal_based_Fermented_Baby_Food_for_Shelf_Life_Prediction/links/5ea6a84b299bf11256128bff/Chemical-Kinetic-Modeling-of-Nutricereal-based-Fermented-Baby-Food-for.
(Continued)

*Primary Examiner* — Talia F Crawley
(74) *Attorney, Agent, or Firm* — FINNEGAN, HENDERSON, FARABOW, GARRETT & DUNNER LLP

(57) ABSTRACT

The disclosure relates generally to methods and systems for predicting a remaining shelf-life of a millet flour using data-driven approach. Conventional techniques for estimating the remaining shelf life of the millet flour are very limited and not effective. The methods and systems of the present disclosure employs a Long short-term memory (LSTM) network architecture-based model to predict the remaining shelf-life of the millet flour based on both the nutritional quality and the rancidity using the information of millet variant and days after milling of the grain. The LSTM network based model is trained on the training data obtained using the chemical reaction kinetic model from the input data comprising a peroxide content, and a fat acidity. The present disclosure predicts the remaining shelf-life of the
(Continued)

millet flour in terms of both the remaining nutritional shelf-life and the remaining rancid shelf-life.

15 Claims, 8 Drawing Sheets

(51) Int. Cl.

| | | |
|---|---|---|
| *G06N 3/0455* | (2023.01) | |
| *G06N 3/09* | (2023.01) | |
| *G16C 20/30* | (2019.01) | |
| *G16C 20/70* | (2019.01) | |
| *G06Q 10/087* | (2023.01) | |

(56) References Cited

U.S. PATENT DOCUMENTS

| | | | |
|---|---|---|---|
| 2020/0251229 A1* | 8/2020 | Rai ....................... | G06V 10/751 |
| 2020/0302377 A1* | 9/2020 | Danducci ............. | G06Q 10/087 |
| 2021/0279857 A1* | 9/2021 | Tong ..................... | G01N 21/80 |
| 2022/0147755 A1* | 5/2022 | Dutta ................... | G06F 18/2413 |
| 2025/0001426 A1* | 1/2025 | Ramasamy ........... | A23L 29/225 |
| 2025/0044271 A1* | 2/2025 | Brouwers .............. | G01N 33/02 |

OTHER PUBLICATIONS

W. Yu et al., "Combining Mechanistic Modelling With Machine Learning in an Industrial Case Study: Predicting Cream Cheese Fermentation," Computer Science, Engineering, 2019, Semantic Scholar, https://folk.ntnu.no/skoge/prost/proceedings/FOPAM_2019/FOPAM%20Contributed%20Papers/33_FinalAbstract.pdf.

Yuanming Chu et al., "Shelf-Life Prediction of Glazed Large Yellow Croaker (Pseudosciaena crocea) during Frozen Storage Based on Arrhenius Model and Long-Short-Term Memory Neural Networks Model," Sustainable Aquaculture and Fisheries, Sep. 10, 2021, MDPI, Basel, Switzerland, https://www.mdpi.com/2410-3888/6/3/39.

Durga Shankar Bunkar et al., "Kinetics of changes in shelf life parameters during storage of pearl millet based kheer mix and development of a shelf life prediction model," J Food Sci Technol, Dec. 11, 2012, vol. 51; Issue: 12, Springer, https://pmc.ncbi.nlm.nih.gov/articles/PMC4252426/pdf/13197_2012_Article_892.pdf.

* cited by examiner

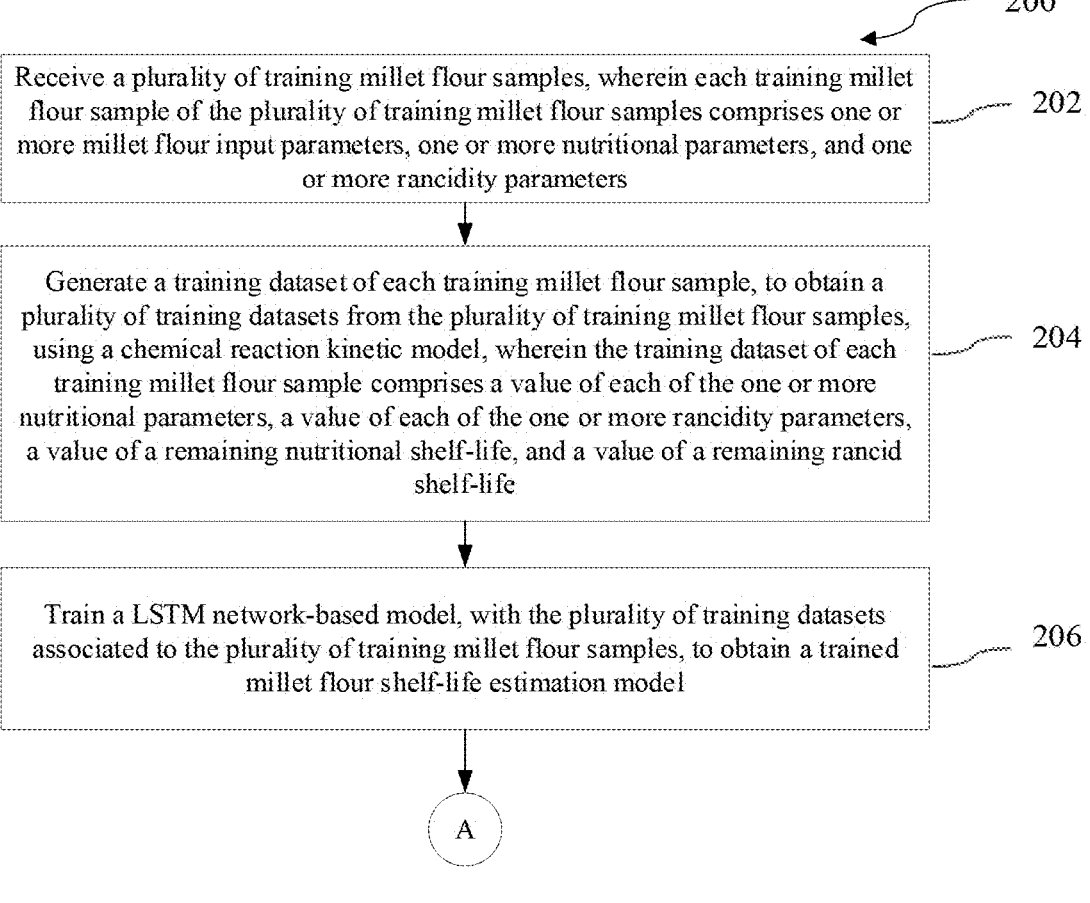

200

Receive a plurality of training millet flour samples, wherein each training millet flour sample of the plurality of training millet flour samples comprises one or more millet flour input parameters, one or more nutritional parameters, and one or more rancidity parameters — 202

Generate a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life — 204

Train a LSTM network-based model, with the plurality of training datasets associated to the plurality of training millet flour samples, to obtain a trained millet flour shelf-life estimation model — 206

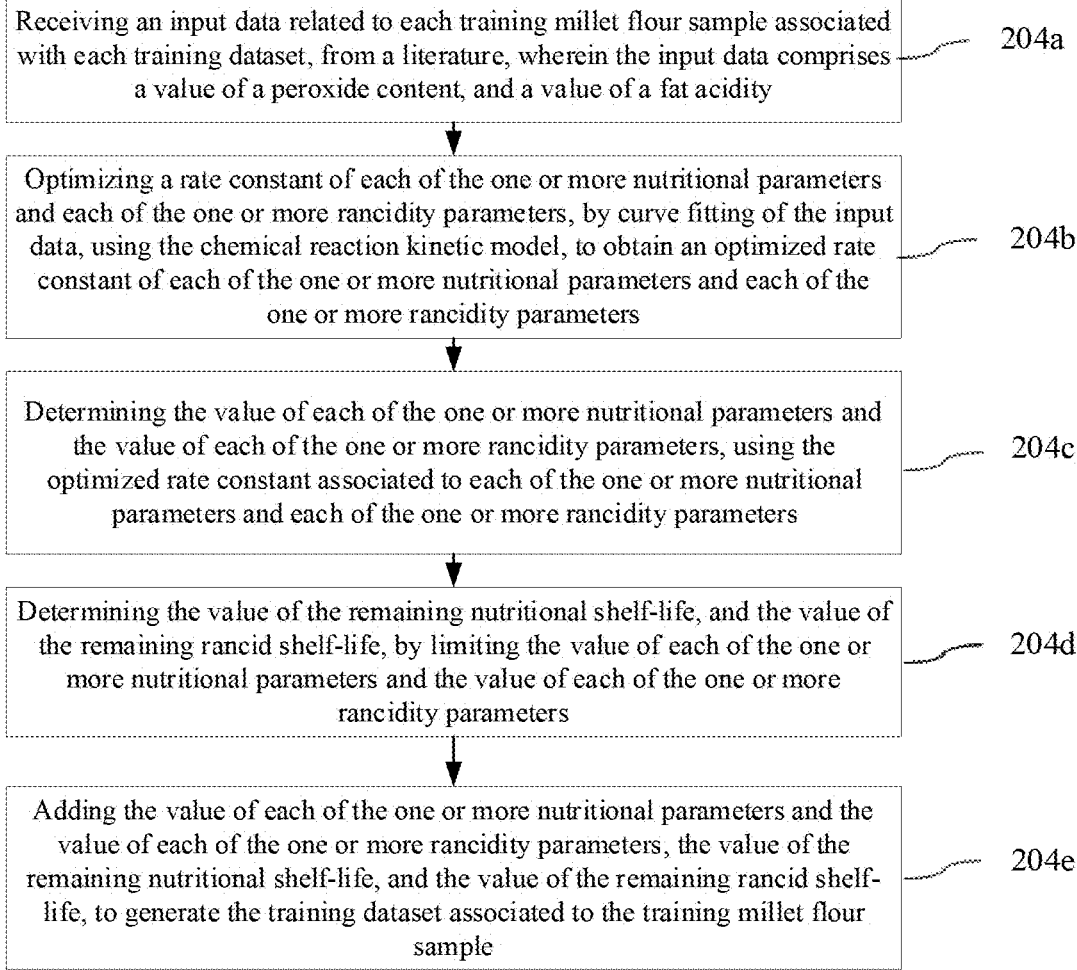

Receiving an input data related to each training millet flour sample associated with each training dataset, from a literature, wherein the input data comprises a value of a peroxide content, and a value of a fat acidity — 204a Optimizing a rate constant of each of the one or more nutritional parameters and each of the one or more rancidity parameters, by curve fitting of the input data, using the chemical reaction kinetic model, to obtain an optimized rate constant of each of the one or more nutritional parameters and each of the one or more rancidity parameters — 204b Determining the value of each of the one or more nutritional parameters and the value of each of the one or more rancidity parameters, using the optimized rate constant associated to each of the one or more nutritional parameters and each of the one or more rancidity parameters — 204c Determining the value of the remaining nutritional shelf-life, and the value of the remaining rancid shelf-life, by limiting the value of each of the one or more nutritional parameters and the value of each of the one or more rancidity parameters — 204d Adding the value of each of the one or more nutritional parameters and the value of each of the one or more rancidity parameters, the value of the remaining nutritional shelf-life, and the value of the remaining rancid shelf-life, to generate the training dataset associated to the training millet flour sample — 204e

FIG. 3

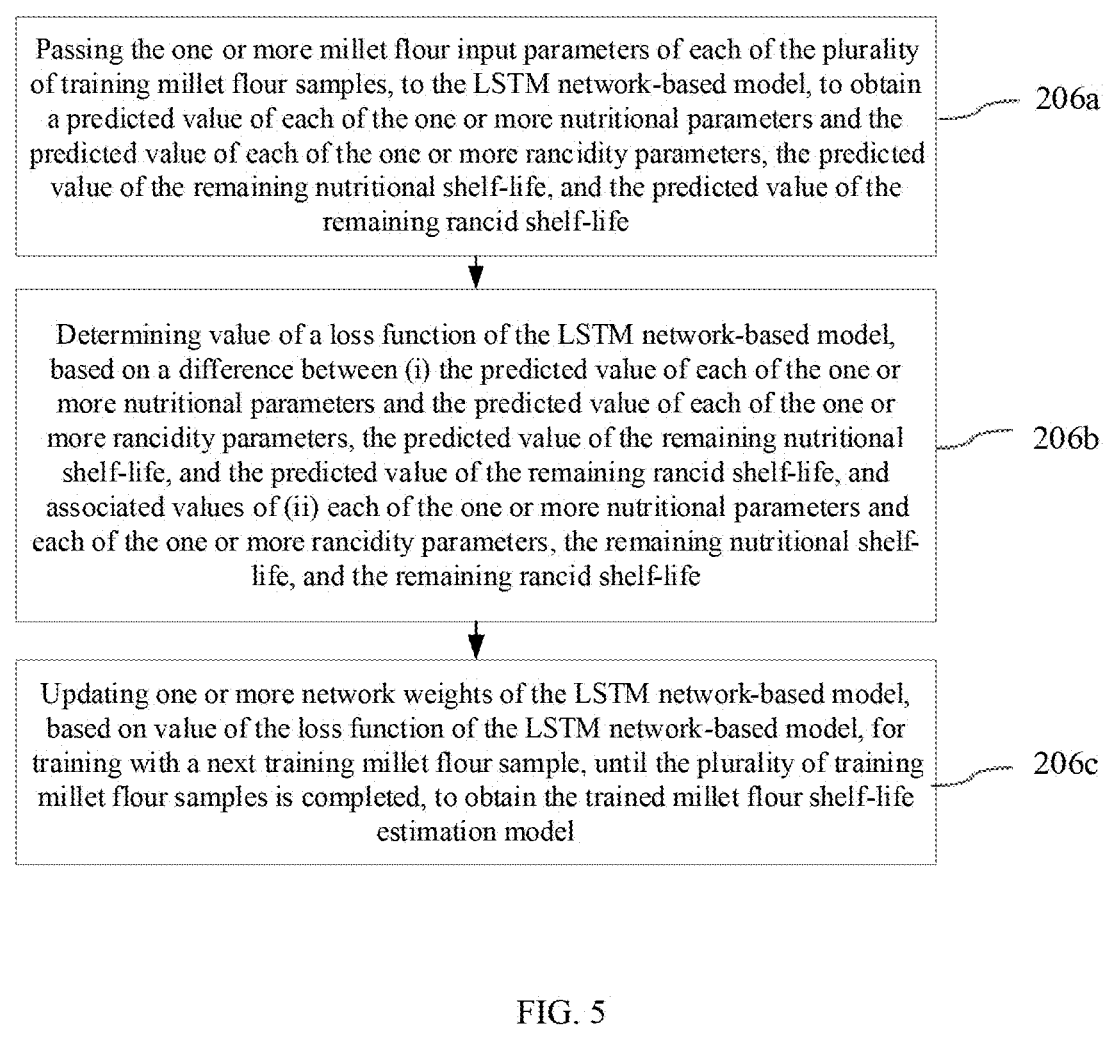

Passing the one or more millet flour input parameters of each of the plurality of training millet flour samples, to the LSTM network-based model, to obtain a predicted value of each of the one or more nutritional parameters and the predicted value of each of the one or more rancidity parameters, the predicted value of the remaining nutritional shelf-life, and the predicted value of the remaining rancid shelf-life ⎯⎯ 206a Determining value of a loss function of the LSTM network-based model, based on a difference between (i) the predicted value of each of the one or more nutritional parameters and the predicted value of each of the one or more rancidity parameters, the predicted value of the remaining nutritional shelf-life, and the predicted value of the remaining rancid shelf-life, and associated values of (ii) each of the one or more nutritional parameters and each of the one or more rancidity parameters, the remaining nutritional shelf-life, and the remaining rancid shelf-life ⎯⎯ 206b Updating one or more network weights of the LSTM network-based model, based on value of the loss function of the LSTM network-based model, for training with a next training millet flour sample, until the plurality of training millet flour samples is completed, to obtain the trained millet flour shelf-life estimation model ⎯⎯ 206c

FIG. 5

METHODS AND SYSTEMS FOR PREDICTING A REMAINING SHELF-LIFE OF A MILLET FLOUR USING DATA-DRIVEN APPROACH

PRIORITY CLAIM

This U.S. patent application claims priority under 35 U.S.C. § 119 to: Indian Patent Application number 202321082073, filed on Dec. 2, 2023. The entire contents of the aforementioned application are incorporated herein by reference.

TECHNICAL FIELD

The disclosure herein generally relates to shelf-life prediction, and, more particularly, to methods and systems for predicting a remaining shelf-life of a millet flour using data-driven approach.

BACKGROUND

Millets have garnered less attention compared to other grains despite being versatile and highly nutritious crops due to poor shelf life of millet-based products like millet flour. The shelf-life constraints stem from significant concerns related to the rancidity and degradation of nutritional value over time in millet flour products. Traditional estimation of shelf life of millet flour-based products has relied on experimental analysis of rancidity indicators, including free fatty acids, acid value, and peroxide value, along with some reaction kinetic models. Advancements in artificial intelligence and computational learning techniques have paved way for the application of machine learning models in predicting the remaining shelf life of the millet flour from the date of milling of grains. However conventional techniques for estimating the remaining shelf life of the millet flour are very limited and not effective as many parameters such as nutritional and rancidity are not considered as a combination.

SUMMARY

Embodiments of the present disclosure present technological improvements as solutions to one or more of the above-mentioned technical problems recognized by the inventors in conventional systems.

In an aspect, a processor-implemented method for predicting a remaining shelf-life of a millet flour using data-driven approach, is provided. The method including the steps of: receiving a plurality of training millet flour samples, wherein each training millet flour sample of the plurality of training millet flour samples comprises one or more millet flour input parameters, one or more nutritional parameters, and one or more rancidity parameters; generating a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life; training a LSTM network-based model, with the plurality of training datasets associated to the plurality of training millet flour samples, to obtain a trained millet flour shelf-life estimation model; receiving the one or more millet flour input parameters of a test millet flour sample; and passing the one or more millet flour input parameters of the test millet flour sample, to the trained millet flour shelf-life estimation model, to estimate the value of the remaining nutritional shelf-life, and the value of the remaining rancid shelf-life of the test millet flour sample.

In another aspect, a system for predicting a remaining shelf-life of a millet flour using data-driven approach is provided. The system includes: a memory storing instructions; one or more Input/Output (I/O) interfaces; and one or more hardware processors coupled to the memory via the one or more I/O interfaces, wherein the one or more hardware processors are configured by the instructions to: receive a plurality of training millet flour samples, wherein each training millet flour sample of the plurality of training millet flour samples comprises one or more millet flour input parameters, one or more nutritional parameters, and one or more rancidity parameters; generate a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life; train a LSTM network-based model, with the plurality of training datasets associated to the plurality of training millet flour samples, to obtain a trained millet flour shelf-life estimation model; receive the one or more millet flour input parameters of a test millet flour sample; and pass the one or more millet flour input parameters of the test millet flour sample, to the trained millet flour shelf-life estimation model, to estimate the value of the remaining nutritional shelf-life, and the value of the remaining rancid shelf-life of the test millet flour sample.

In yet another aspect, there are provided one or more non-transitory machine-readable information storage mediums comprising one or more instructions which when executed by one or more hardware processors cause: receiving a plurality of training millet flour samples, wherein each training millet flour sample of the plurality of training millet flour samples comprises one or more millet flour input parameters, one or more nutritional parameters, and one or more rancidity parameters; generating a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life; training a LSTM network-based model, with the plurality of training datasets associated to the plurality of training millet flour samples, to obtain a trained millet flour shelf-life estimation model; receiving the one or more millet flour input parameters of a test millet flour sample; and passing the one or more millet flour input parameters of the test millet flour sample, to the trained millet flour shelf-life estimation model, to estimate the value of the remaining nutritional shelf-life, and the value of the remaining rancid shelf-life of the test millet flour sample.

In an embodiment, the one or more millet flour input parameters of each of the plurality of training millet flour samples comprises (i) a millet flour variant of a plurality of millet flour variants, and (ii) a number of hours after milling of the millet flour variant of the plurality of millet flour variants, the one or more nutritional parameters comprises an unsaturated fatty acid concentration, and the one or more rancidity parameters comprises (i) a fat acidity, and (ii) a peroxide content.

In an embodiment, generating the training dataset of each training millet flour sample, to obtain the plurality of training datasets from the plurality of training millet flour samples, using the chemical reaction kinetic model, comprising: receiving an input data related to each training millet flour sample associated with each training dataset, from a literature, wherein the input data comprises a value of a peroxide content, and a value of a fat acidity; optimizing a rate constant of each of the one or more nutritional parameters and each of the one or more rancidity parameters, by curve fitting of the input data, using the chemical reaction kinetic model, to obtain an optimized rate constant of each of the one or more nutritional parameters and each of the one or more rancidity parameters; determining the value of each of the one or more nutritional parameters and the value of each of the one or more rancidity parameters, using the optimized rate constant associated to each of the one or more nutritional parameters and each of the one or more rancidity parameters; determining the value of the remaining nutritional shelf-life, and the value of the remaining rancid shelf-life, by limiting the value of each of the one or more nutritional parameters and the value of each of the one or more rancidity parameters; and adding the value of each of the one or more nutritional parameters and the value of each of the one or more rancidity parameters, the value of the remaining nutritional shelf-life, and the value of the remaining rancid shelf-life, to generate the training dataset associated to the training millet flour sample.

In an embodiment, training the LSTM network-based model, with the plurality of training datasets associated to the plurality of training millet flour samples, to obtain the trained millet flour shelf-life estimation model, comprising: passing the one or more millet flour input parameters of each of the plurality of training millet flour samples, to the LSTM network-based model, to obtain a predicted value of each of the one or more nutritional parameters and the predicted value of each of the one or more rancidity parameters, the predicted value of the remaining nutritional shelf-life, and the predicted value of the remaining rancid shelf-life; determining value of a loss function of the LSTM network-based model, based on a difference between (i) the predicted value of each of the one or more nutritional parameters and the predicted value of each of the one or more rancidity parameters, the predicted value of the remaining nutritional shelf-life, and the predicted value of the remaining rancid shelf-life, and associated values of (ii) each of the one or more nutritional parameters and each of the one or more rancidity parameters, the remaining nutritional shelf-life, and the remaining rancid shelf-life; and updating one or more network weights of the LSTM network-based model, based on value of the loss function of the LSTM network-based model, for training with a training millet flour sample, until the plurality of training millet flour samples is completed, to obtain the trained millet flour shelf-life estimation model.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIGS. 2A-2B illustrate exemplary flow diagrams of a processor-implemented method for predicting a remaining shelf-life of a millet flour using data-driven approach, using the system of FIG. 1, in accordance with some embodiments of the present disclosure.

FIG. 3 is a flow diagram showing steps for generating the training dataset of each training millet flour sample, to obtain the plurality of training datasets from the plurality of training millet flour samples, using the chemical reaction kinetic model, in accordance with some embodiments of the present disclosure.

FIG. 5 is a flow diagram showing steps for training the LSTM network-based model, with the plurality of training datasets associated to the plurality of training millet flour samples, to obtain the trained millet flour shelf-life estimation model, in accordance with some embodiments of the present disclosure.

DETAILED DESCRIPTION

Figure 1:
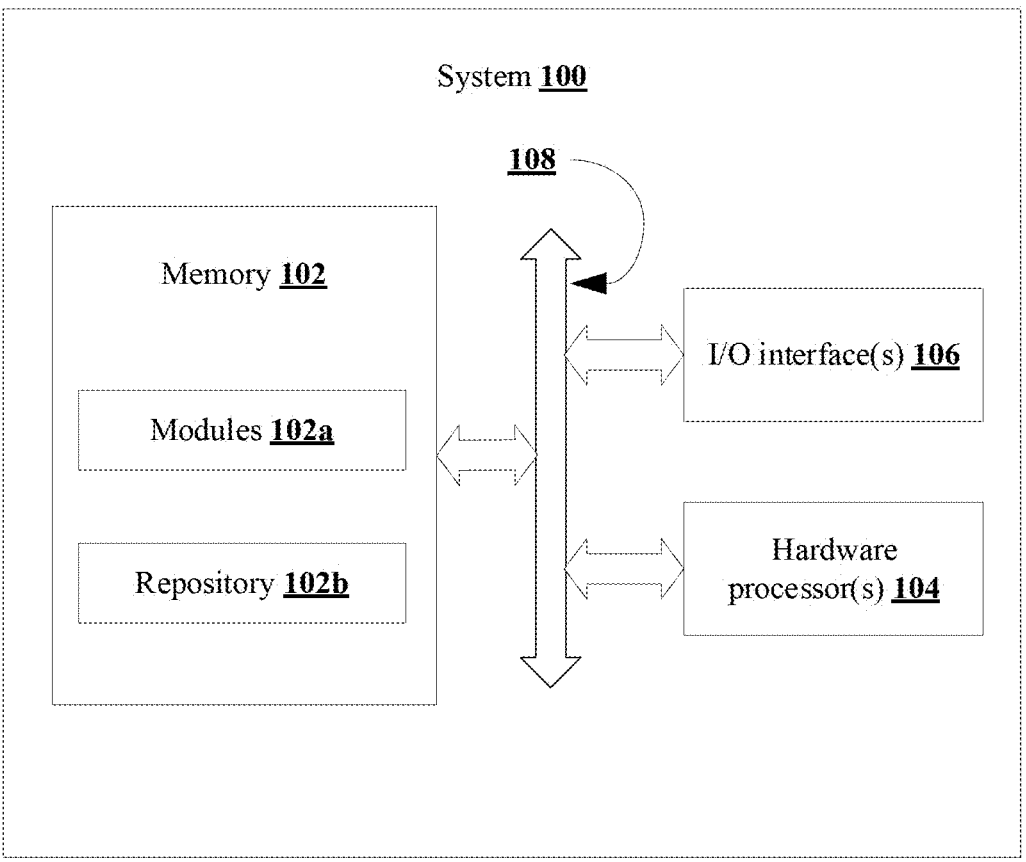
FIG. 1 is an exemplary block diagram of a system for predicting a remaining shelf-life of a millet flour using data-driven approach, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Millets are a group of small-seeded grasses that have been cultivated for thousands of years in many parts of the world, particularly in Asia and Africa. They are sturdy and adaptable crops that can thrive in various settings and are perfectly suited for low-input agricultural systems, showcasing their ability to flourish with minimal resources. According to the Food and Agriculture Organization (FAO), the world production of millet is 89.17 million metric tons from an area of 74 million ha. According to some of the study, India is the global leader in production of millets with a share of around 15% of the world total production. Millets are also highly nutritious, containing significant amounts of proteins, fiber, vitamins, and other important nutrients making them highly suitable for daily consumption. Despite their benefits, millets have received relatively less attention as compared to other crops. One of the key reasons behind this is the poor shelf-life of millet-based products.

Shelf-life refers to the period during which a product can be stored without compromising its safety and nutritional content. Perishability or shelf-life of a food product is affected by unfavorable storage conditions like excessive heat or humidity. Millet flour is a valuable food source due to its high nutritional content, but its short shelf life due to lipid oxidation and rancidity off-odor generation during storage limits its utilization. Rancidity is caused by the presence of fatty acids, enzyme activity, and other factors, leading to off-flavor generation during storage. Rancidity parameters like free fatty acid, acid value and peroxide value have been used to detect the shelf-life and study oxidation-kinetics in various products made from lipid-containing grain.

In addition to rancidity, the decline in the nutritional value of millet products during storage is also a noticeable issue. For example, nutritionally, pearl millet flour is a good source of energy, quality protein, vitamins, minerals, crude fibers, antioxidants, and fat. Pearl Millets have a fat content of approximately 5.4 grams per 100 grams of flour and are rich in unsaturated fatty acids (UFA), constituting up to 74% of the total fat content. These millets contain significant amounts of nutritionally valuable omega-3 fatty acids, including oleic acid (25%), linoleic acid (45%), and linolenic acid (4%). These fatty acids are of great importance and play a vital role in maintaining optimal health.

Hence, millet flour-based products, known for being a healthier alternative to other grain-based products, have a specific nutritional shelf-life. Beyond this point, millet flour-based products may not offer superior nutritional benefits compared to alternative options. Unsaturated fatty acid or lipid concentration can be a good indicator to predict the nutritional shelf-life, if not the best. At present, the estimation of millet flour remaining shelf-life primarily relies on experimental analysis of rancidity indicators such as peroxide value, free fatty acids, and fat acidity. Additionally, reaction kinetic models are commonly employed as an alternative approach to predict the remaining shelf-life of millet flour products. These models provide a quantitative assessment of the deterioration process over time, allowing for the estimation of how long millet flour can be stored before significant quality degradation occurs. Though kinetic models have been useful in predicting the remaining shelf-life, food degradation involves complex reaction mechanisms that require many assumptions to develop a simplified kinetic model.

Additionally, these models often assume consistent reaction kinetics throughout the entire deterioration process, which is not always accurate. In contrast, computational learning techniques can offer a more effective approach by analyzing experimental data to comprehend quality degradation patterns and make accurate predictions, without relying heavily on such assumptions.

With the advancement in Artificial Intelligence (AI) and computational learning techniques, few researchers have previously attempted to use machine learning (ML) models to predict the remaining shelf-life using rancidity indicators. Researchers have employed Feed Forward Neural Network (FFNN) to predict the different rancidity indicators of pearl millet grains and millet biscuits. FFNN is a powerful method to capture the non-linearity between the input and output variables. But the main shortcoming of FFNN model is that it lacks memory and therefore is less suitable for time-series or sequential data. Additionally, a considerable amount of data is required to train the FFNN to understand the patterns.

Long Short-Term Memory (LSTM) Network architecture has been employed to address the limitations encountered in the FFNNs in literature. Previous studies have demonstrated comparison between Arrhenius and LSTM neural network model. However, the Long Short-Term Memory (LSTM)

Network architecture is not fully utilized to predict the remaining shelf-life of the millet flour using the available chemical and nutritional parameters.

The present disclosure solves the technical problems in the art with the methods and systems for predicting a remaining shelf-life of a millet flour using data-driven approach. In the present disclosure, fat acidity and a peroxide content are utilized as an indicator for rancid shelf-life, while unsaturated fatty acid concentration serves as a predictor for nutritional shelf-life of the millet flour. A Long short-term memory (LSTM) network architecture-based model is employed to predict the remaining shelf-life of the millet flour based on both the nutritional quality and the rancidity using the information of millet variant and days after milling of the grain.

Referring now to the drawings, and more particularly to FIG. 1 through FIG. 6B, where similar reference characters denote corresponding features consistently throughout the figures, there are shown preferred embodiments and these embodiments are described in the context of the following exemplary system and/or method.

FIG. 1 is an exemplary block diagram of a system 100 for predicting a remaining shelf-life of a millet flour using data-driven approach, in accordance with some embodiments of the present disclosure. In an embodiment, the system 100 includes or is otherwise in communication with one or more hardware processors 104, communication interface device(s) or input/output (I/O) interface(s) 106, and one or more data storage devices or memory 102 operatively coupled to the one or more hardware processors 104. The one or more hardware processors 104, the memory 102, and the I/O interface(s) 106 may be coupled to a system bus 108 or a similar mechanism.

The I/O interface(s) 106 may include a variety of software and hardware interfaces, for example, a web interface, a graphical user interface (GUI), and the like. The I/O interface(s) 106 may include a variety of software and hardware interfaces, for example, interfaces for peripheral device(s), such as a keyboard, a mouse, an external memory, a plurality of sensor devices, a printer and the like. Further, the I/O interface(s) 106 may enable the system 100 to communicate with other devices, such as web servers and external databases.

The I/O interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface(s) 106 may include one or more ports for connecting a number of computing systems with one another or to another server computer. Further, the I/O interface(s) 106 may include one or more ports for connecting a number of devices to one another or to another server.

The one or more hardware processors 104 may be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In the context of the present disclosure, the expressions 'processors' and 'hardware processors' may be used interchangeably. In an embodiment, the system 100 can be implemented in a variety of computing systems, such as laptop computers, portable computers, notebooks, hand-held devices, worksta-
tions, mainframe computers, servers, a network cloud and
the like.

The memory 102 may include any computer-readable
medium known in the art including, for example, volatile
memory, such as static random access memory (SRAM) and
dynamic random access memory (DRAM), and/or non-
volatile memory, such as read only memory (ROM), eras-
able programmable ROM, flash memories, hard disks, opti-
cal disks, and magnetic tapes. In an embodiment, the
memory 102 includes a plurality of modules 102a and a
repository 102b for storing data processed, received, and
generated by one or more of the plurality of modules 102a.
The plurality of modules 102a may include routines, pro-
grams, objects, components, data structures, and so on,
which perform particular tasks or implement particular
abstract data types.

The plurality of modules 102a may include programs or
computer-readable instructions or coded instructions that
supplement applications or functions performed by the sys-
tem 100. The plurality of modules 102a may also be used as,
signal processor(s), state machine(s), logic circuitries, and/
or any other device or component that manipulates signals
based on operational instructions. Further, the plurality of
modules 102a can be used by hardware, by computer-
readable instructions executed by the one or more hardware
processors 104, or by a combination thereof. In an embodi-
ment, the plurality of modules 102a can include various
sub-modules (not shown in FIG. 1). Further, the memory
102 may include information pertaining to input(s)/output(s)
of each step performed by the processor(s) 104 of the system
100 and methods of the present disclosure.

The repository 102b may include a database or a data
engine. Further, the repository 102b amongst other things,
may serve as a database or includes a plurality of databases
for storing the data that is processed, received, or generated
as a result of the execution of the plurality of modules 102a.
Although the repository 102b is shown internal to the system
100, it will be noted that, in alternate embodiments, the
repository 102b can also be implemented external to the
system 100, where the repository 102b may be stored within
an external database (not shown in FIG. 1) communicatively
coupled to the system 100. The data contained within such
external database may be periodically updated. For example,
data may be added into the external database and/or existing
data may be modified and/or non-useful data may be deleted
from the external database. In one example, the data may be
stored in an external system, such as a Lightweight Direc-
tory Access Protocol (LDAP) directory and a Relational
Database Management System (RDBMS). In another
embodiment, the data stored in the repository 102b may be
distributed between the system 100 and the external data-
base.

Figure 2B:
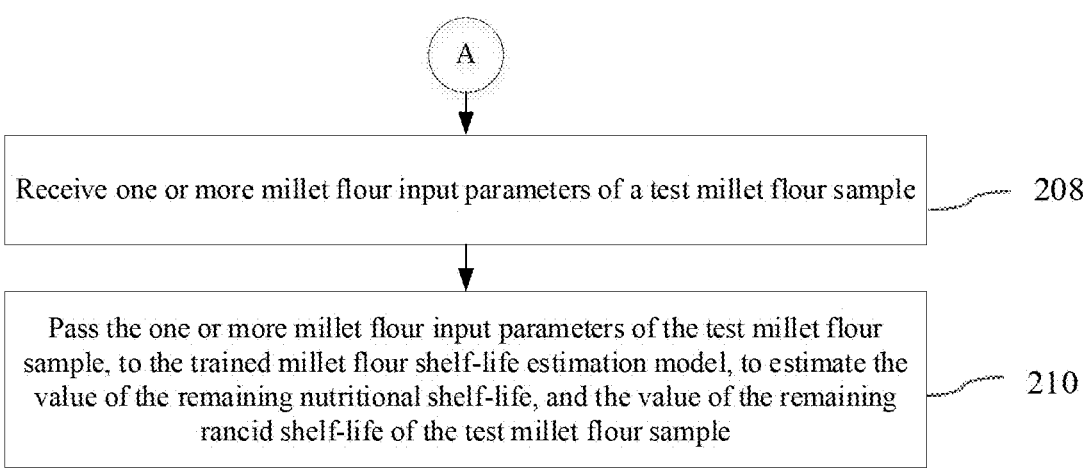

Referring to FIGS. 2A-2B, components and functionali-
ties of the system 100 are described in accordance with an
example embodiment of the present disclosure. For
example, FIGS. 2A-2B illustrate exemplary flow diagrams
of a processor-implemented method 200 for predicting a
remaining shelf-life of a millet flour using data-driven
approach, using the system 100 of FIG. 1, in accordance
with some embodiments of the present disclosure. Although
the steps of the method 200 shown in FIGS. 2A-2B includ-
ing process steps, method steps, techniques or the like may
be described in a sequential order, such processes, methods,
and techniques may be configured to work in alternate
orders. In other words, any sequence or order of steps that
may be described does not necessarily indicate a requirement that the steps be performed in that order. The steps of
processes described herein may be performed in any prac-
tical order. Further, some steps may be performed simulta-
neously, or some steps may be performed alone or indepen-
dently.

At step 202 of the method 200, the one or more hardware
processors 104 of the system 100 are configured to receive
a plurality of training millet flour samples. The plurality of
training millet flour samples is associated with a plurality of
millet flour variants. In an embodiment, the plurality of
millet flour variants includes millet flours obtained from
different millet variants of a given millet type. For example,
if the given millet type is pearl millet, then the different
millet variants include but is not limited to HHB 226,
Sulkhaniya Bajra, BJ 104, RHB 173, PAC 909, and 86M64.
In an embodiment, the millet flour is a flour of the given
millet type selected from a list but is not limited to Finger
Millet (Ragi), Foxtail Millet (Kakum/Kangni), Sorghum
Millet (Jowar), Pearl Millet (Bajra), Buckwheat Millet
(Kuttu), Amaranth Millet (Rajgira/Ramdana/Chola), Little
Millet (Moraiyo/Kutki/Shavan/Sama), Barnyard Millet, and
Broomcorn Millet.

Each training millet flour sample of the plurality of
training millet flour samples includes one or more millet
flour input parameters, one or more nutritional parameters,
and one or more rancidity parameters. In an embodiment,
the one or more millet flour input parameters of each training
millet flour sample includes a millet flour variant of the
plurality of millet flour variants, and a number of hours after
milling of the millet flour variant. In an embodiment, the one
or more nutritional parameters of each training millet flour
sample include an unsaturated fatty acid concentration of the
associated millet flour sample. In an embodiment, the one or
more rancidity parameters of each training millet flour
sample include a fat acidity, and a peroxide content of the
associated millet flour sample.

At step 204 of the method 200, the one or more hardware
processors 104 of the system 100 are configured to generate
a training dataset of each training millet flour sample, to
obtain a plurality of training datasets from the plurality of
training millet flour samples. In an embodiment, a chemical
reaction kinetic model is employed to generate the training
dataset for each training millet flour sample. In an embodi-
ment, the training dataset of each training millet flour sample
comprises a value of each of the one or more nutritional
parameters, the value of each of the one or more rancidity
parameters, the value of a remaining nutritional shelf-life,
and the value of a remaining rancid shelf-life.

FIG. 3 is a flow diagram showing steps for generating the
training dataset of each training millet flour sample, to
obtain the plurality of training datasets from the plurality of
training millet flour samples, using the chemical reaction
kinetic model, in accordance with some embodiments of the
present disclosure. As shown in FIG. 3, generating the
training dataset of each training millet flour sample, to
obtain the plurality of training datasets from the plurality of
training millet flour samples, using the chemical reaction
kinetic model, is explained in detail through steps 204a to
204e.

Machine Learning/Deep learning models require large
amounts of data to predict the desired output variable with
a decent accuracy. Since the available data from the litera-
ture was insufficient to train and test the models effectively,
the chemical reaction kinetic model is employed to generate
additional data.

At step 204a, an input data related to each training millet
flour sample associated with each training dataset, is received, from a literature. In an embodiment, the input data includes a value of peroxide content, and the value of the fat acidity.

At step 204b, a rate constant of each of the one or more nutritional parameters and each of the one or more rancidity parameters, is optimized by curve fitting of the input data, using the chemical reaction kinetic model, to obtain an optimized rate constant of each of the one or more nutritional parameters and each of the one or more rancidity parameters.

At step 204c, the value of each of the one or more nutritional parameters and the value of each of the one or more rancidity parameters, are determined using the optimized rate constant associated to each of the one or more nutritional parameters and each of the one or more rancidity parameters obtained at step 204b.

The chemical reaction kinetic model accounts for peroxidation of the unsaturated fatty acid/lipids.

$$\text{Unsaturated fatty acid } (UFA) \rightarrow \text{Peroxide } (PV) \rightarrow \text{Volatiles} \qquad (1)$$

$$\frac{d[UFA]}{dt} = -k_1[UFA] \qquad (2)$$

$$[UFA] = [UFA]_0\left(e^{-k_1 t}\right) \qquad (3)$$

$$\frac{d[PV]}{dt} = k_1[UFA] - k_2[PV] \qquad (4)$$

$$[PV] = [UFA]_0\left(\frac{k_1}{k_2 - k_1}\right)\left(e^{-k_1 t} - e^{-k_2 t}\right) \qquad (5)$$

Wherein $k_1$ and $k_2$ are rate constants of decomposition of UFA and the decomposition of peroxide respectively.

Hydroperoxide formation and decomposition was modelled as a first-order series reaction. The chemical reaction kinetic model used here corroborates the change in concentration of peroxide reported in literature. The Levenberg-Marquardt algorithm was utilized to optimize the parameter values for rate constants $k_1$ (decomposition of UFA) and k2 (decomposition of peroxide), ensuring the best fit between the curve and the data. Concentrations of the species are normalized prior to parameter optimization. Kinetic rate constant values for low-rancid and high-rancid variant of pearl millet were obtained separately. The time-series data for unsaturated fatty acid concentration and peroxide value are generated by using equations (3) and (5) on Python tool.

The fat acidity, another key rancidity indicator, is modelled using the zero-order kinetics model mentioned as equation 6:

$$\frac{d[FA]}{dt} = k_3 \qquad (6)$$

Wherein $k_3$ is a rate constant of decomposition of fat acidity.

At step 204d, the value of the remaining nutritional shelf-life, and the value of the remaining rancid shelf-life, are determined by limiting the value of each of the one or more nutritional parameters and the value of each of the one or more rancidity parameters.

In an embodiment, the concentration of UFAs in refined flour is used as a limiting value to determine the remaining nutritional shelf-life of the millet flour. Equation 7 represents the remaining nutritional shelf-life according to the limiting value of unsaturated fatty acid (UFA) concentration.

$$RSL_{rancid} = \ln\left(\frac{[UFA]}{[UFA]_{lim}}\right) \qquad (7)$$

In an embodiment, the fat acidity and peroxide content are used as the limiting value for determining the remaining rancid shelf-life. These values are chosen based on the criteria used in the development of Rancidity Matrix for high rancid variants. Equation 8 is used to determine the remaining rancid shelf-life based on whichever threshold, the peroxide content value or the fat acidity, is reached first.

$$RSL_{rancid} = t_{[PVlim/FAlim]} - t \qquad (8)$$

Finally at step 204e, the value of each of the one or more nutritional parameters and the value of each of the one or more rancidity parameters, obtained at step 204c, and the value of the remaining nutritional shelf-life and the value of the remaining rancid shelf-life obtained at step 204d, are added as a set to generate the training dataset associated to the training millet flour sample. Likewise, the training dataset associated to each training millet flour sample is generated to obtain the plurality of training datasets from the plurality of training millet flour samples.

At step 206 of the method 200, the one or more hardware processors 104 of the system 100 are configured to train the LSTM network-based model, with the plurality of training datasets associated to the plurality of training millet flour samples, generated at step 204 of the method 200, to obtain a trained millet flour shelf-life estimation model.

The chemical reaction kinetic model is used at step 204 of method 200 to generate the plurality of training datasets and train the Long Short-Term Memory network (LSTM). The purpose of this generated training datasets is to demonstrate the performance of LSTM network architecture and compare it with the conventional FFNN. In practical applications, the LSTM network architecture employed here could utilize real experimental data to predict the remaining shelf-life.

The Long Short-Term Memory Networks (LSTMs) are extensions of Recurrent Neural Network, designed to model sequential data and are better suited for time series analysis. The time-series values for the fat-acidity, the unsaturated fatty acid concentration, the remaining rancidity shelf-life, and the remaining nutritional shelf-life are included in the dataset used as a training input to the LSTM model.

Figure 4:
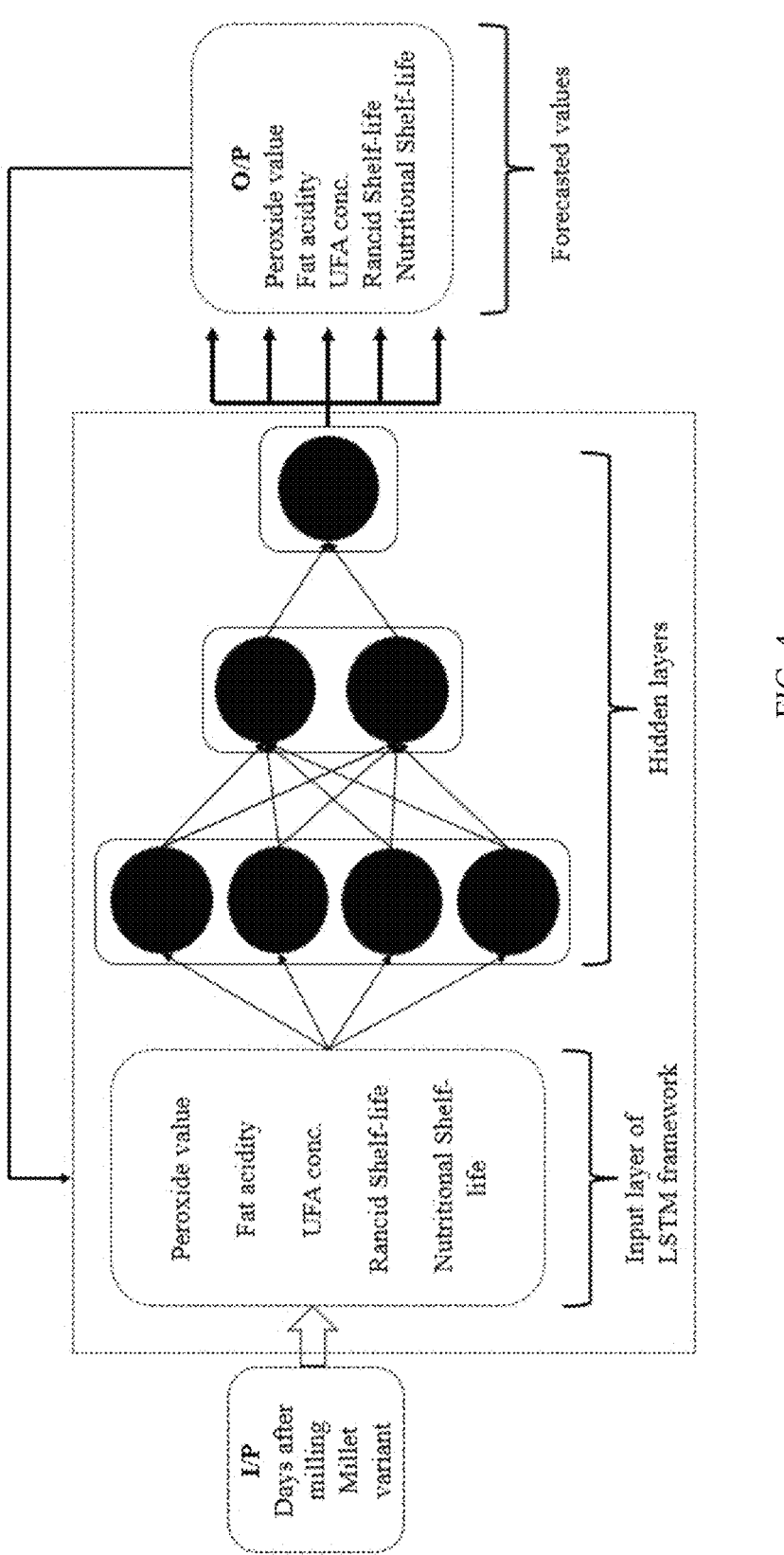
FIG. 4 is an exemplary architecture diagram of the LSTM network-based model, in accordance with some embodiments of the present disclosure.

FIG. 4 is an exemplary architecture diagram of the LSTM network-based model, in accordance with some embodiments of the present disclosure. As shown in FIG. 4, the LSTM network-based model is presented as a sequential model which is structured with flour LSTM layers, each having a different number of units. Specifically, the first LSTM layer comprises 256 units, followed by a layer with 128 units, another with 64 units, and the final LSTM layer with 32 units. After each LSTM layer, there is a ReLU activation layer. The last LSTM layer is succeeded by a Dense layer that produces a single output for prediction.

FIG. 5 is a flow diagram showing steps for training the LSTM network-based model, with the plurality of training datasets associated to the plurality of training millet flour samples, to obtain the trained millet flour shelf-life estimation model, in accordance with some embodiments of the present disclosure. As shown in FIG. 5, training the LSTM network-based model, with the plurality of training datasets associated to the plurality of training millet flour samples, to obtain the trained millet flour shelf-life estimation model, is explained in detail through steps 206a to 206c.

At step 206a, the one or more millet flour input parameters of each training millet flour sample, are passed to the LSTM network-based model, to obtain a predicted value of each of the one or more nutritional parameters and the predicted value of each of the one or more rancidity parameters, the predicted value of the remaining nutritional shelf-life, and the predicted value of the remaining rancid shelf-life.

At step 206b, value of a loss function of the LSTM network-based model, is calculated. In an embodiment, the value of loss function of the LSTM network-based model is calculated based on a difference between (i) the predicted value of each of the one or more nutritional parameters and the predicted value of each of the one or more rancidity parameters, the predicted value of the remaining nutritional shelf-life, and the predicted value of the remaining rancid shelf-life, and associated values of (ii) each of the one or more nutritional parameters and each of the one or more rancidity parameters, the remaining nutritional shelf-life, and the remaining rancid shelf-life. The loss function of the LSTM network-based model is defined as a mean square function between the (i) the predicted value of each of the one or more nutritional parameters and the associated value of each of the one or more nutritional parameters (actual values), (ii) the predicted value of each of the one or more rancidity parameters and the associated value of each of the one or more rancidity parameters, (iii) the predicted value of the remaining nutritional shelf-life and the associated value of the remaining nutritional shelf-life, and (iv) the predicted value of the remaining rancid shelf-life and the associated value of the remaining rancid shelf-life.

At step 206c, one or more network weights of the LSTM network-based model, are updated based on the value of loss function of the LSTM network-based model, for training with a next training millet flour sample. The training process is continued until the plurality of training millet flour samples is completed, to obtain the trained millet flour shelf-life estimation model.

The LSTM network model is trained with the dataset for an initial 120 hours for different millet variants to predict future values. The exemplary training time of 120 hours. To predict the remaining shelf-life of the subsequent days, the trained millet flour shelf-life estimation model is used. Following the training, the trained millet flour shelf-life estimation model predicts the fat acidity, the unsaturated fatty acid concentration, the peroxide content, the remaining rancidity shelf-life, and the remaining nutritional shelf-life for subsequent days.

At step 208 of the method 200, the one or more hardware processors 104 of the system 100 are configured to receive the one or more millet flour input parameters of a test millet flour sample whose remaining shelf-life is to be estimated.

At step 210 of the method 200, the one or more hardware processors 104 of the system 100 are configured to pass the one or more millet flour input parameters of the test millet flour sample received at step 208 of the method 200, to the trained millet flour shelf-life estimation model, to estimate the value of the remaining nutritional shelf-life, and the value of the remaining rancid shelf-life of the test millet flour sample.

The methods and systems of the present disclosure predict the remaining shelf-life of the millet flour in terms of both the remaining nutritional shelf-life and the remaining rancid shelf-life. As the LSTM based network model is employed in the present disclosure, the trained millet flour shelf-life estimation model obtained accurately predicts the remaining shelf-life for the required period as a time-series data. Hence the users can effectively select the millet flour-based products based on the remaining shelf-life.

Example Scenario:

An end-to-to end example is explained below to generate the obtain the plurality of training datasets from the plurality of training millet flour samples using the chemical reaction kinetic model to obtain the trained millet flour shelf-life estimation model which is used to estimate the value of the remaining nutritional shelf-life, and the value of the remaining rancid shelf-life of the millet flour sample. Further the results of the present disclosure using the LSTM network-based model are compared with results of the conventional FFNN based model to show the performance of the methods and systems of the present disclosure.

Data Curation:

The input data of millet flour samples to generate the training dataset utilized in the model development, was collected from existing literature sources. Six distinct variants of pearl millet were used for the analysis. The study focuses on the analysis of Pearl Millet flour from six distinct variants. Among these six variants, two of them were characterized as low rancid variants, namely HHB 226 and Sulkhaniya Bajra. Conversely, the remaining flour variants, namely BJ 104, RHB 173, PAC 909, and 86M84, were classified as high-rancid variants. The input data collected from the literature contains time series values of peroxide content, values for fat acidity at day 0 and day 10. All the collected data was at the temperature of 25° C. stored in air-tight zipped packaging.

Table 1 shows the exemplary input data containing time series values of peroxide content (meq. $O_2$/kg flour).

TABLE 1

| Millet Variant | Day 0 | Day 5 | Day 10 | Day 15 | Day 20 | Day 25 | Day 30 |
|---|---|---|---|---|---|---|---|
| HHB 226 | 20 | 50 | 80 | 72 | 64 | 58 | 48 |
| Sulkhaniya Bajra | 20 | 56 | 82 | 78 | 75 | 63 | 58 |
| BJ 104 | 40 | 86 | 110 | 100 | 95 | 86 | 82 |
| RHB 173 | 50 | 90 | 108 | 104 | 95 | 88 | 82 |
| PAC 909 | 50 | 75 | 100 | 88 | 80 | 75 | 70 |
| 86M64 | 30 | 70 | 100 | 90 | 80 | 76 | 71 |

Table 2 shows the exemplary input data containing contains time series values of the fat acidity (mg NaOH/g flour at Day 0 and Day 10).

TABLE 2

| Millet Variant | Day 0 | Day 10 |
|---|---|---|
| HHB 226 | 2.00 ± 0.2 | 2.80 ± 0.2 |
| Sulkhaniya Bajra | 5.12 ± 0.1 | 6.90 ± 0.4 |
| BJ 104 | 6.50 ± 0.2 | 10.00 ± 0.4 |
| RHB 173 | 3.80 ± 0.4 | 6.12 ± 0.4 |
| PAC 909 | 2.80 ± 0.1 | 5.20 ± 0.1 |
| 86M64 | 3.20 ± 0.2 | 6.80 ± 0.1 |

Chemical Reaction Kinetic Model for Data Generation:

The Levenberg-Marquardt algorithm was utilized to optimize the parameter values for rate constants $k_1$ (decomposition of UFA) and $k_2$ (decomposition of peroxide), ensuring the best fit between the curve and the data (Table 1). Concentrations of the species were normalized prior to parameter optimization. Kinetic rate constant values for low-rancid and high-rancid variant of pearl millet were obtained separately. The time-series data for unsaturated fatty acid concentration and peroxide value were generated by using kinetic model equations (3) and (5) on Python tool. The fat acidity was modelled using the zero-order kinetics model using equation (6).

According to the Food and Agriculture Organization (FAO), refined wheat flour, which is considered a poor source of unsaturated fatty acids, contains about 1.5 g of monounsaturated fatty acids (MUFAs)/polyunsaturated fatty acids (PUFAs) per 100 g of flour. Millet flour becomes less nutritious over time as the UFA concentrations decrease due to peroxidation. The concentration of UFAs in refined wheat flour was used as a limiting value to determine the nutritional shelf-life of pearl millet. Equation 7 was used to determine the remaining nutritional shelf-life according to the limiting value of unsaturated fatty acid concentration. The fat acidity of 7.5 mg NaOH/g flour and peroxide content of 100 meq. $O_2$/kg flour were used as the limiting value for rancid shelf-life detection. These values were chosen based on the criteria used in the development of Rancidity Matrix for high rancid variants. Equation 8 was used to determine the remaining rancid shelf life based on whichever threshold, the peroxide content value, or the fat acidity, is reached first.

Feed Forward Neural Network Model and Long Short-Term Memory Network Model:

The Feed Forward neural networks utilized in this study included two input features: the number of days after milling and the name of the variant. It also had three hidden layers and five output variables, which were peroxide content, fat acidity, unsaturated fatty acid concentration, rancidity, and nutritional shelf-life. By using this structure, the model aimed to analyze and predict these variables based on the input data. The entire dataset was categorized into 80% training and 20% validation, and testing. The number of neurons in each hidden layer were chosen using hyperparameter tuning. The network performance was evaluated by mean squared error (MSE), mean absolute error (MAE) and coefficient of determination ($R^2$).

The LSTM network model of the present disclosure was trained with the dataset for an initial 120 hours for six various millet variants to predict future values. The choice of training time of 120 hours is based on a comparison study. To predict the remaining shelf-life of subsequent days. By leveraging the power of LSTM network architecture, a model was built which predicts the peroxide value, the fat acidity, the unsaturated fatty acid concentration, the remaining rancid shelf-life and the remaining nutritional shelf-life using millet variant and days after milling as the user input.

Training Data Generation:

In Eq (1) and (2), $k_1$ and $k_2$ values were obtained for one variant in each low-rancid and high-rancid group accurately predicted peroxide values for other variants in their respective groups (Table 3). The concentrations of unsaturated fatty acid (UFA) in fresh pearl millet flour are typically ~5.5 g/100 g of flour. Time-series data for unsaturated fatty acid concentration were generated using the average value of 4 g/100 g of pearl millet flour (~74% of 5.4 g/100 g of fresh flour) as the initial value for UFA concentration and $k_1$ (rate constant for decomposition of Unsaturated Fatty acid). Table 3 shows the predicted $R^2$ using rate constants obtained from the curve-fitting:

TABLE 3

| Type of Variant | Variant used for curve-fitting | Rate constants | Variants used prediction | $R^2_{predicted}$ |
|---|---|---|---|---|
| Low Rancid | HHB 226 | $k_1 = 1.95$, $k_2 = 2.13$ | Sulkhaniya Bajra | 0.91 |
| High Rancid | BJ 104 | $k_1 = 0.85$, $k_2 = 4.24$ | RHB 173 | 0.92 |
| | | | PAC 909 | 0.90 |
| | | | 86M64 | 0.81 |

Using the initial concentration and the concentration on the 10th day, the eq (4) rate constant (3) was calculated for six different variants and time-series data for fat acidity were generated. The remaining shelf-life was calculated using fat-acidity and peroxide content as rancidity indicators and unsaturated fatty acid concentration as a nutritional indicator.

Comparison Study for Optimum Value of Training Days:

The experiment conducted with varying training durations revealed that the optimal training time for achieving the best results was determined to be 5 days. The averaged mean squared error of the limiting shelf-life based on all six variants consistently decreased until the initial 5 days of training, after which any further changes were insignificant. Here, the limiting shelf-life means the lesser shelf-life between nutritional and rancid shelf-life.

Comparison Between FFNN and LSTM Network Architecture:

The fat acidity and peroxide content were used as rancidity indicators and unsaturated fatty acid lipid concentration was used as a nutritional indicator in the current study. These indicators were used to predict rancidity and nutritional shelf-life respectively. Fat acidity of 7.5 mg NaOH/g flour, Peroxide value of 100 meq. $O_2$/kg flour and unsaturated fatty acid lipid concentration of 1.5 g/100 g flour were used as threshold limiting values above which the flour was deemed unfit for human consumption. The FFNN and LSTM network architecture (the present disclosure) were used to predict the remaining shelf life. And to evaluate the performance of the models, mean squared error (MSE) was employed as the chosen loss function.

The performance evaluation of the FFNN (conventional) and LSTM (present disclosure) are shown in table 4 and table 5 respectively.

TABLE 4

| Millet Variant | Parameter | MSE | MAE | $R^2$ |
|---|---|---|---|---|
| HHB 226 | Nutritional Shelf-life | 0.0911 | 0.3011 | 0.983 |
| | Rancid Shelf-life | 0.0009 | 0.0285 | 0.925 |
| | Fat Acidity | 0.0001 | 0.0029 | 0.9927 |
| | Unsaturated Fatty Acid Conc. | 1.3205 | 1.1482 | 0.9931 |
| | Peroxide Value | 0.8304 | 0.7617 | 0.9957 |
| Sulkhaniya Bajra | Nutritional Shelf-life | 0.0708 | 0.2095 | 0.9893 |
| | Rancid Shelf-life | 0.0001 | 0.0053 | 0.9963 |
| | Fat Acidity | 0.0001 | 0.0075 | 0.9912 |
| | Unsaturated Fatty Acid Conc. | 0.5256 | 0.6032 | 0.9973 |
| | Peroxide Value | 0.9985 | 0.9987 | 0.9948 |
| BJ104 | Nutritional Shelf-life | 0.1105 | 0.2635 | 0.9809 |
| | Rancid Shelf-life | 0.0004 | 0.0193 | 0.9783 |
| | Fat Acidity | 0.0001 | 0.0058 | 0.9983 |
| | Unsaturated Fatty Acid Conc. | 1.1135 | 1.045 | 0.9942 |

TABLE 4-continued

| Millet Variant | Parameter | MSE | MAE | $R^2$ |
|---|---|---|---|---|
| | Peroxide Value | 7.0828 | 1.9388 | 0.9631 |
| RHB173 | Nutritional Shelf-life | 0.027 | 0.147 | 0.9941 |
| | Rancid Shelf-life | 0.0001 | 0.0072 | 0.9963 |
| | Fat Acidity | 0.0003 | 0.015 | 0.9858 |
| | Unsaturated Fatty Acid Conc. | 0.7869 | 0.7835 | 0.9959 |
| | Peroxide Value | 1.2297 | 1.1053 | 0.9936 |
| PAC909 | Nutritional Shelf-life | 0.0078 | 0.0754 | 0.9973 |
| | Rancid Shelf-life | 0.0001 | 0.0029 | 0.9992 |
| | Fat Acidity | 0.0001 | 0.0089 | 0.9954 |
| | Unsaturated Fatty Acid Conc. | 3.698 | 1.4236 | 0.9807 |
| | Peroxide Value | 2.5927 | 1.57 | 0.9865 |
| 86M64 | Nutritional Shelf-life | 0.2389 | 0.3758 | 0.9615 |
| | Rancid Shelf-life | 0.0001 | 0.0061 | 0.9978 |
| | Fat Acidity | 0.0001 | 0.0088 | 0.9917 |
| | Unsaturated Fatty Acid Conc. | 0.4082 | 0.5618 | 0.9979 |
| | Peroxide Value | 0.6707 | 0.7034 | 0.9965 |

TABLE 5

| Millet Variant | Parameter | MSE | MAE | $R^2$ |
|---|---|---|---|---|
| HHB226 | Rancid Shelf-life | 8.9822 | 1.7179 | 0.9363 |
| | Nutritional Shelf-life | 16.2519 | 2.3221 | 0.9072 |
| | Fat Acidity | 0.1324 | 0.234 | 0.9464 |
| | Unsaturated Fatty Acid Conc. | 0.1682 | 0.3335 | 0.9178 |
| | Peroxide Value | 5.9425 | 1.2437 | 0.9827 |
| Sulkhaniya Bajra | Rancid Shelf-life | 17.5403 | 2.7402 | 0.9432 |
| | Nutritional Shelf-life | 11.5036 | 2.3908 | 0.9109 |
| | Fat Acidity | 2.0344 | 1.0654 | 0.8647 |
| | Unsaturated Fatty Acid Conc. | 0.2072 | 0.3572 | 0.8625 |
| | Peroxide Value | 6.4225 | 1.4462 | 0.8325 |
| 86M64 | Rancid Shelf-life | 8.2394 | 1.7337 | 0.9783 |
| | Nutritional Shelf-life | 2.8526 | 1.0262 | 0.9825 |
| | Fat Acidity | 2.1660 | 1.078 | 0.9019 |
| | Unsaturated Fatty Acid Conc. | 0.4072 | 0.5572 | 0.8729 |
| | Peroxide Value | 5.6690 | 1.4820 | 0.8125 |
| BJ104 | Rancid Shelf-life | 15.0457 | 2.6606 | 0.934 |
| | Nutritional Shelf-life | 14.2581 | 2.6131 | 0.9361 |
| | Fat Acidity | 2.6230 | 1.2821 | 0.8940 |
| | Unsaturated Fatty Acid Conc. | 0.3990 | 0.5230 | 0.8492 |
| | Peroxide Value | 6.5710 | 1.8890 | 0.8015 |
| RHB173 | Rancid Shelf-life | 11.892 | 2.2375 | 0.9187 |
| | Nutritional Shelf-life | 15.4647 | 2.1331 | 0.9092 |
| | Fat Acidity | 3.150 | 1.230 | 0.8819 |
| | Unsaturated Fatty Acid Conc. | 0.4128 | 0.6120 | 0.8552 |
| | Peroxide Value | 6.8620 | 1.8815 | 0.7920 |
| PAC909 | Rancid Shelf-life | 16.7063 | 2.1805 | 0.9570 |
| | Nutritional Shelf-life | 20.24 | 2.9973 | 0.94845 |
| | Fat Acidity | 3.2290 | 1.5875 | 0.8769 |
| | Unsaturated Fatty Acid Conc. | 0.3678 | 0.4994 | 0.9090 |
| | Peroxide Value | 5.1780 | 1.2230 | 0.8225 |

The results indicate that the LSTM network architecture of the present disclosure outperforms the FFNN model architecture in predicting the shelf-life of pearl millet flour. When using the LSTM network, the mean squared error (MSE), mean absolute error (MAE), and R-$^{squared}$ ($R^2$) values for predicting the nutritional shelf-life range from 0.865 to 2.4283, 0.759 to 1.3255, and 0.9869 to 0.9967, respectively. Similarly, the MSE, MAE, and $R^2$ values for predicting the rancid shelf-life range from 1.219-3.378, 0.9232-1.2456, and 0.9894-0.9950, respectively. On the other hand, when using the FFNN model, the MSE, MAE, and $R^2$ values for predicting the nutritional shelf-life range from 2.8526-20.24, 1.0262-2.9973, and 0.9092-0.9825, respectively. Similarly, the MSE, MAE, and $R^2$ values for predicting the rancid shelf-life range from 8.2394-17.5403, 1.7179-2.6606, and 0.9187-0.9783, respectively.

Figure 6A:
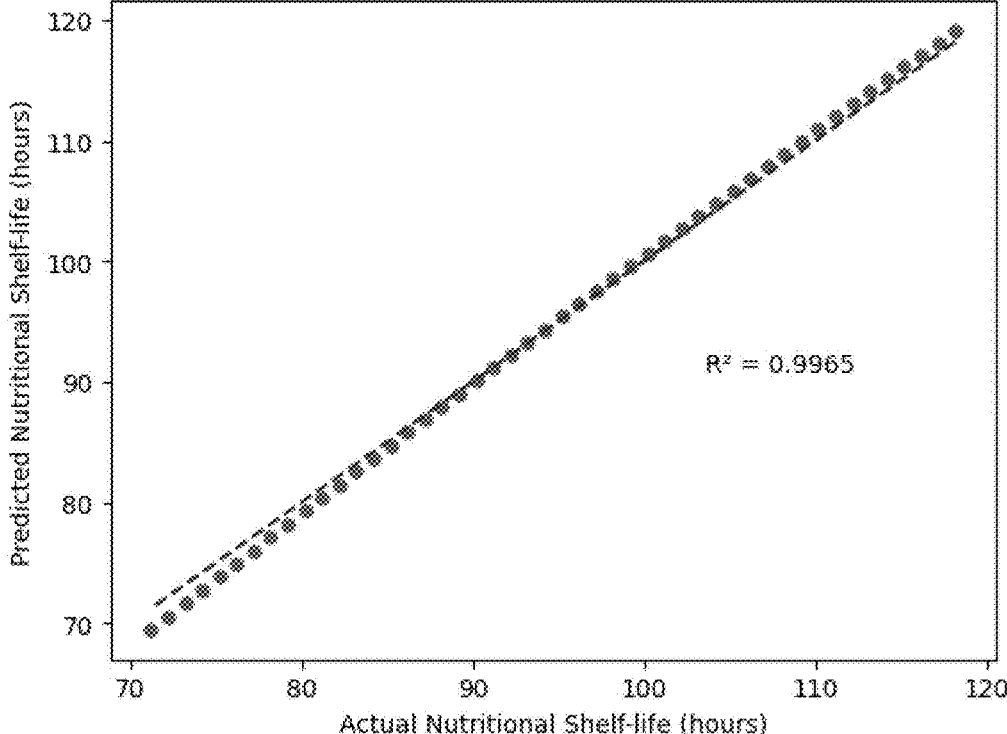
FIG. 6A is a graph showing a comparison of an actual remaining nutritional shelf-life and the predicted remaining nutritional shelf-life obtained by the trained millet flour shelf-life estimation model, for a pearl millet flour variant of 86M64, in accordance with some embodiments of the present disclosure.
Figure 6B:
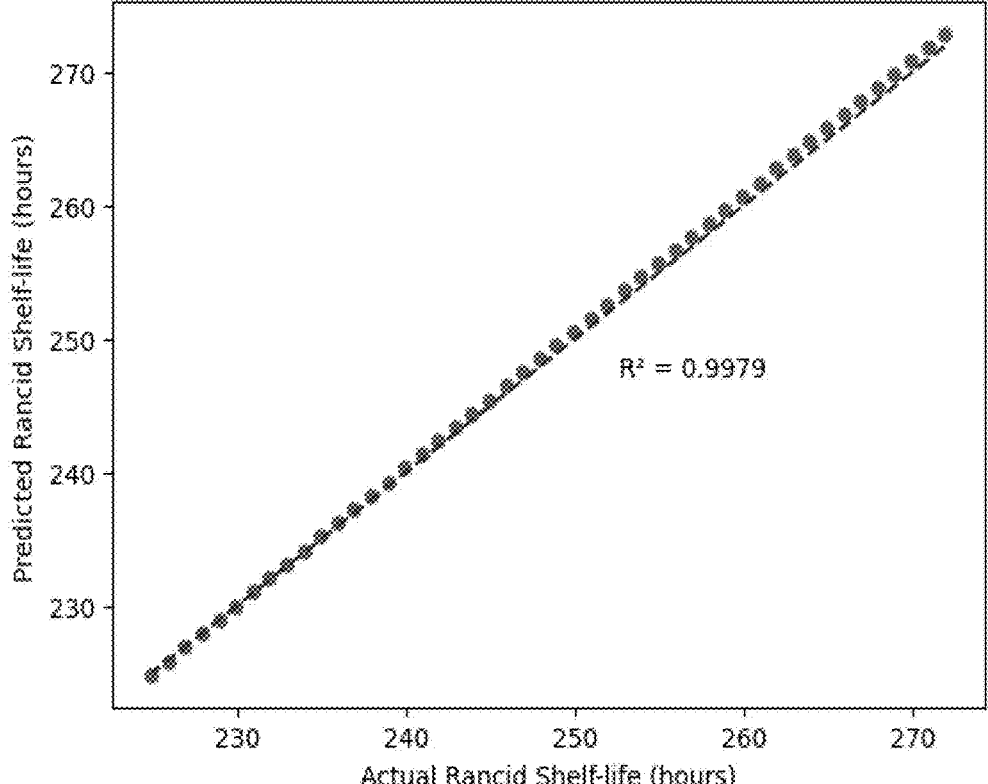
FIG. 6B is a graph showing a comparison of an actual remaining rancid shelf-life and the predicted remaining rancid shelf-life obtained by the trained millet flour shelf-life estimation model, for a pearl millet flour variant of 86M64, in accordance with some embodiments of the present disclosure.

FIG. 6A is a graph showing a comparison of an actual remaining nutritional shelf-life and the predicted remaining nutritional shelf-life obtained by the trained millet flour shelf-life estimation model, for a pearl millet flour variant of 86M64, in accordance with some embodiments of the present disclosure. FIG. 6B is a graph showing a comparison of an actual remaining rancid shelf-life and the predicted remaining rancid shelf-life obtained by the trained millet flour shelf-life estimation model, for a pearl millet flour variant of 86M64, in accordance with some embodiments of the present disclosure. From FIGS. 6A and 6B, both the predicted remaining nutritional shelf-life and the predicted remaining rancid shelf-life obtained by the trained millet flour shelf-life estimation model are almost similar to the associated actual values.

Further, the predictions of nutritional and rancid shelf-life from LSTM network architecture-based model were compared with ground truth (shown in Table 6 and Table 7 respectively). The positive value of remaining shelf life indicates the number of days left for the flour to be used safely, while the negative value indicates the number of days past the safe shelf-life.

TABLE 6

| Days after milling | Millet Variant | Variant Type | Actual remaining shelf-life (days) | Predicted remaining shelf-life (days) | Error (days) |
|---|---|---|---|---|---|
| 10 | HHB 226 | Low Rancid | 3.79 | 3.59 | 0.2 |
| 11 | HHB 226 | Low Rancid | 2.84 | 2.65 | 0.19 |
| 10 | Sulkhaniya Bajra | Low Rancid | 4.54 | 4.38 | 0.16 |
| 11 | Sulkhaniya Bajra | Low Rancid | 3.57 | 3.18 | 0.41 |
| 10 | BJ 104 | High Rancid | −4.22 | −5.11 | 0.91 |
| 11 | BJ 104 | High Rancid | −5.22 | −5.92 | 0.7 |
| 10 | RHB 173 | High Rancid | −3.58 | −3.92 | 0.34 |
| 11 | RHB 173 | High Rancid | −4.58 | −4.77 | 0.19 |
| 10 | PAC 909 | High Rancid | −2.22 | −1.63 | −0.59 |
| 11 | PAC 909 | High Rancid | −2.82 | −2.36 | −0.46 |

TABLE 7

| Days after milling | Millet Variant | Variant Type | Actual remaining shelf-life (days) | Predicted remaining shelf-life (days) | Error (days) |
|---|---|---|---|---|---|
| 10 | Sulkhaniya Bajra | Low Rancid | 6.17 | 6.13 | 0.04 |
| 12 | Sulkhaniya Bajra | Low Rancid | 4.17 | 4.29 | −0.12 |
| 10 | BJ 104 | High Rancid | −5.72 | −6.57 | 0.85 |

TABLE 7-continued

| Days after milling | Millet Variant | Variant Type | Actual remaining shelf-life (days) | Predicted remaining shelf-life (days) | Error (days) |
|---|---|---|---|---|---|
| 12 | BJ 104 | High Rancid | −7.72 | −7.46 | −0.26 |
| 10 | RHB173 | High Rancid | −4.12 | −4.78 | 0.64 |
| 12 | RHB173 | High Rancid | −6.12 | −5.98 | −0.14 |

The results also demonstrate that the rancid shelf-life is not consistently the limiting factor for pearl millet flour. In certain cases, the nutritional shelf-life expires before the rancid shelf-life. The shelf-life of high-rancid millet variants were found to be limited by rancidity whereas the shelf-life of low-rancid millet variants were found to be limited by poor nutritional value.

Application/Use Case:

The assessment of nutritional quality and shelf-life in millets and millet-derived products holds significant importance for manufacturers, retailers, and consumers. Predicting these parameters would yield substantial benefits for stakeholders involved in the millet industry. The model developed in this work has been implemented as a web-based application to predict these parameters utilizing input data on 1) hours after milling and 2) specific millet variant. This web application also assists various customers to choose millet products based on daily dietary recommendations depending on age group, gender, pregnancy etc.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problems of predicting the remaining shelf-life of the millet flour using data-driven approach. In the experimental results, shelf-life of pearl millet flour of 6 various variants was predicted using rancidity (fat acidity and peroxide content) and nutritional indicator (Unsaturated fatty acid concentration). The study shows that the LSTM network works well in estimating the shelf-life of pearl millet flour with high accuracy when the model is trained with data of initial 5 days. Notably, the results indicated that in some cases nutritional shelf-life is a better way to estimate that the food is unfit for consumption as compared to the shelf-life estimated using rancidity parameters. Furthermore, the study found that the LSTM outperformed the Feed Forward Neural Network (FFNN) in predicting the shelf-life of the various variants of pearl millet flour. The developed model holds promising potential for accurately forecasting the shelf-life of different variants of pearl millet flour. This study also demonstrates the significance of considering the nutritional shelf-life as an important factor when discussing the shelf-life of millet flour-based products.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
receiving, via one or more hardware processors, a plurality of training millet flour samples, wherein each training millet flour sample of the plurality of training millet flour samples comprises one or more millet flour input parameters, one or more nutritional parameters, and one or more rancidity parameters;
generating, via the one or more hardware processors, a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life; and
training, via the one or more hardware processors, a LSTM network-based model, with the plurality of training datasets associated to the plurality of training millet flour samples, to obtain a trained millet flour shelf-life estimation model.

2. The processor implemented method of claim 1, further comprising:
receiving, via the one or more hardware processors, one or more millet flour input parameters of a test millet flour sample; and
passing, via the one or more hardware processors, the one or more millet flour input parameters of the test millet flour sample, to the trained millet flour shelf-life estimation model, to estimate the value of the remaining nutritional shelf-life, and the value of the remaining rancid shelf-life of the test millet flour sample.

3. The processor implemented method of claim 1, wherein:
the one or more millet flour input parameters of each of the plurality of training millet flour samples comprises (i) a millet flour variant of a plurality of millet flour variants, and (ii) a number of hours after milling of the millet flour variant of the plurality of millet flour variants,
the one or more nutritional parameters comprises an unsaturated fatty acid concentration, and
the one or more rancidity parameters comprises (i) a fat acidity, and (ii) a peroxide content.

4. The processor implemented method of claim 1, wherein generating the training dataset of each training millet flour sample, to obtain the plurality of training datasets from the plurality of training millet flour samples, using the chemical reaction kinetic model, comprising:
receiving an input data related to each training millet flour sample associated with each training dataset, from a literature, wherein the input data comprises a value of a peroxide content, and a value of a fat acidity;
optimizing a rate constant of each of the one or more nutritional parameters and each of the one or more rancidity parameters, by curve fitting of the input data, using the chemical reaction kinetic model, to obtain an optimized rate constant of each of the one or more nutritional parameters and each of the one or more rancidity parameters;

20 determining the value of each of the one or more nutritional parameters and the value of each of the one or more rancidity parameters, using the optimized rate constant associated to each of the one or more nutritional parameters and each of the one or more rancidity parameters;
determining the value of the remaining nutritional shelf-life, and the value of the remaining rancid shelf-life, by limiting the value of each of the one or more nutritional parameters and the value of each of the one or more rancidity parameters; and
adding the value of each of the one or more nutritional parameters and the value of each of the one or more rancidity parameters, the value of the remaining nutritional shelf-life, and the value of the remaining rancid shelf-life, to generate the training dataset associated to the training millet flour sample.

5. The processor implemented method of claim 1, wherein training the LSTM network-based model, with the plurality of training datasets associated to the plurality of training millet flour samples, to obtain the trained millet flour shelf-life estimation model, comprising:
passing the one or more millet flour input parameters of each of the plurality of training millet flour samples, to the LSTM network-based model, to obtain a predicted value of each of the one or more nutritional parameters and the predicted value of each of the one or more rancidity parameters, the predicted value of the remaining nutritional shelf-life, and the predicted value of the remaining rancid shelf-life;
determining value of a loss function of the LSTM network-based model, based on a difference between (i) the predicted value of each of the one or more nutritional parameters and the predicted value of each of the one or more rancidity parameters, the predicted value of the remaining nutritional shelf-life, and the predicted value of the remaining rancid shelf-life, and associated values of (ii) each of the one or more nutritional parameters and each of the one or more rancidity parameters, the remaining nutritional shelf-life, and the remaining rancid shelf-life; and
updating one or more network weights of the LSTM network-based model, based on value of the loss function of the LSTM network-based model, for training with a next training millet flour sample, until the plurality of training millet flour samples is completed, to obtain the trained millet flour shelf-life estimation model.

6. A system, comprising:
a memory storing instructions;
one or more input/output (I/O) interfaces; and
one or more hardware processors coupled to the memory via the one or more I/O interfaces, wherein the one or more hardware processors are configured by the instructions to:
receive a plurality of training millet flour samples, wherein each training millet flour sample of the plurality of training millet flour samples comprises one or more millet flour input parameters, one or more nutritional parameters, and one or more rancidity parameters;
generate a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life; and train a LSTM network-based model, with the plurality of training datasets associated to the plurality of training millet flour samples, to obtain a trained millet flour shelf-life estimation model.

7. The system of claim 6, wherein the one or more hardware processors are further configured to:

receive the one or more millet flour input parameters of a test millet flour sample; and pass the one or more millet flour input parameters of the test millet flour sample, to the trained millet flour shelf-life estimation model, to estimate the value of the remaining nutritional shelf-life, and the value of the remaining rancid shelf-life of the test millet flour sample.

8. The system of claim 6, wherein:

the one or more millet flour input parameters of each of the plurality of training millet flour samples comprises (i) a millet flour variant of a plurality of millet flour variants, and (ii) a number of hours after milling of the millet flour variant of the plurality of millet flour variants, the one or more nutritional parameters comprises an unsaturated fatty acid concentration, and the one or more rancidity parameters comprises (i) a fat acidity, and (ii) a peroxide content.

9. The system of claim 6, wherein the one or more hardware processors are configured to generate the training dataset of each training millet flour sample, to obtain the plurality of training datasets from the plurality of training millet flour samples, using the chemical reaction kinetic model, by:

receiving an input data related to each training millet flour sample associated with each training dataset, from a literature, wherein the input data comprises a value of a peroxide content, and a value of a fat acidity;

optimizing a rate constant of each of the one or more nutritional parameters and each of the one or more rancidity parameters, by curve fitting of the input data, using the chemical reaction kinetic model, to obtain an optimized rate constant of each of the one or more nutritional parameters and each of the one or more rancidity parameters;

determining the value of each of the one or more nutritional parameters and the value of each of the one or more rancidity parameters, using the optimized rate constant associated to each of the one or more nutritional parameters and each of the one or more rancidity parameters;

determining the value of the remaining nutritional shelf-life, and the value of the remaining rancid shelf-life, by limiting the value of each of the one or more nutritional parameters and the value of each of the one or more rancidity parameters; and adding the value of each of the one or more nutritional parameters and the value of each of the one or more rancidity parameters, the value of the remaining nutritional shelf-life, and the value of the remaining rancid shelf-life, to generate the training dataset associated to the training millet flour sample.

10. The system of claim 6, wherein the one or more hardware processors are configured to train the LSTM network-based model, with the plurality of training datasets associated to the plurality of training millet flour samples, to obtain the trained millet flour shelf-life estimation model, by:

passing the one or more millet flour input parameters of each of the plurality of training millet flour samples, to the LSTM network-based model, to obtain a predicted value of each of the one or more nutritional parameters and the predicted value of each of the one or more rancidity parameters, the predicted value of the remaining nutritional shelf-life, and the predicted value of the remaining rancid shelf-life;

determining value of a loss function of the LSTM network-based model, based on a difference between (i) the predicted value of each of the one or more nutritional parameters and the predicted value of each of the one or more rancidity parameters, the predicted value of the remaining nutritional shelf-life, and the predicted value of the remaining rancid shelf-life, and associated values of (ii) each of the one or more nutritional parameters and each of the one or more rancidity parameters, the remaining nutritional shelf-life, and the remaining rancid shelf-life; and updating one or more network weights of the LSTM network-based model, based on value of the loss function of the LSTM network-based model, for training with a next training millet flour sample, until the plurality of training millet flour samples is completed, to obtain the trained millet flour shelf-life estimation model.

11. One or more non-transitory machine-readable information storage mediums comprising one or more instructions which when executed by one or more hardware processors, cause:

receiving a plurality of training millet flour samples, wherein each training millet flour sample of the plurality of training millet flour samples comprises one or more millet flour input parameters, one or more nutritional parameters, and one or more rancidity parameters;

generating a training dataset of each training millet flour sample, to obtain a plurality of training datasets from the plurality of training millet flour samples, using a chemical reaction kinetic model, wherein the training dataset of each training millet flour sample comprises a value of each of the one or more nutritional parameters, a value of each of the one or more rancidity parameters, a value of a remaining nutritional shelf-life, and a value of a remaining rancid shelf-life; and training a LSTM network-based model, with the plurality of training datasets associated to the plurality of training millet flour samples, to obtain a trained millet flour shelf-life estimation model.

12. The one or more non-transitory machine-readable information storage mediums of claim 11, comprising the one or more instructions which when executed by the one or more hardware processors further cause:

receiving one or more millet flour input parameters of a test millet flour sample; and passing the one or more millet flour input parameters of the test millet flour sample, to the trained millet flour shelf-life estimation model, to estimate the value of the remaining nutritional shelf-life, and the value of the remaining rancid shelf-life of the test millet flour sample.

13. The one or more non-transitory machine-readable information storage mediums of claim 11, wherein:

the one or more millet flour input parameters of each of
the plurality of training millet flour samples comprises
(i) a millet flour variant of a plurality of millet flour
variants, and (ii) a number of hours after milling of the
millet flour variant of the plurality of millet flour
variants,
the one or more nutritional parameters comprises an
unsaturated fatty acid concentration, and
the one or more rancidity parameters comprises (i) a fat
acidity, and (ii) a peroxide content.

14. The one or more non-transitory machine-readable
information storage mediums of claim 11, wherein generating the training dataset of each training millet flour sample,
to obtain the plurality of training datasets from the plurality
of training millet flour samples, using the chemical reaction
kinetic model, comprising:
receiving an input data related to each training millet flour
sample associated with each training dataset, from a
literature, wherein the input data comprises a value of
a peroxide content, and a value of a fat acidity;
optimizing a rate constant of each of the one or more
nutritional parameters and each of the one or more
rancidity parameters, by curve fitting of the input data,
using the chemical reaction kinetic model, to obtain an
optimized rate constant of each of the one or more
nutritional parameters and each of the one or more
rancidity parameters;
determining the value of each of the one or more nutritional parameters and the value of each of the one or
more rancidity parameters, using the optimized rate
constant associated to each of the one or more nutritional parameters and each of the one or more rancidity
parameters;
determining the value of the remaining nutritional shelf-
life, and the value of the remaining rancid shelf-life, by
limiting the value of each of the one or more nutritional
parameters and the value of each of the one or more
rancidity parameters; and adding the value of each of the one or more nutritional
parameters and the value of each of the one or more
rancidity parameters, the value of the remaining nutritional shelf-life, and the value of the remaining rancid
shelf-life, to generate the training dataset associated to
the training millet flour sample.

15. The one or more non-transitory machine-readable
information storage mediums of claim 11, wherein training
the LSTM network-based model, with the plurality of training datasets associated to the plurality of training millet flour
samples, to obtain the trained millet flour shelf-life estimation model, comprising:
passing the one or more millet flour input parameters of
each of the plurality of training millet flour samples, to
the LSTM network-based model, to obtain a predicted
value of each of the one or more nutritional parameters
and the predicted value of each of the one or more
rancidity parameters, the predicted value of the remaining nutritional shelf-life, and the predicted value of the
remaining rancid shelf-life;
determining value of a loss function of the LSTM network-based model, based on a difference between (i)
the predicted value of each of the one or more nutritional parameters and the predicted value of each of the
one or more rancidity parameters, the predicted value
of the remaining nutritional shelf-life, and the predicted
value of the remaining rancid shelf-life, and associated
values of (ii) each of the one or more nutritional
parameters and each of the one or more rancidity
parameters, the remaining nutritional shelf-life, and the
remaining rancid shelf-life; and
updating one or more network weights of the LSTM
network-based model, based on value of the loss function of the LSTM network-based model, for training
with a next training millet flour sample, until the
plurality of training millet flour samples is completed,
to obtain the trained millet flour shelf-life estimation
model.

* * * * *